(12) United States Patent
Gronemann et al.

(10) Patent No.: US 12,024,485 B2
(45) Date of Patent: Jul. 2, 2024

(54) PROCESS AND PLANT FOR PRODUCING METHANOL FROM HYDROGEN-RICH SYNTHESIS GAS

(71) Applicant: L'Air Liquide Société Anonyme pour l'Etude et l'Exploitation des Procédés Georges Claude, Paris (FR)

(72) Inventors: Veronika Gronemann, Karben (DE); Stephan Haase, Steinbach (DE); Lutz Janko, Erzhausen (DE); Hans Kopetsch, Bad Homburg (DE); Chin Han Lim, Frankfurt am Main (DE)

(73) Assignee: L'Air Liquide, Societe Anonyme Pour l'Etude et l'Exploitation des Procedes Georges Claude, Paris (FR)

( * ) Notice: Subject to any disclaimer, the term of this patent is extended or adjusted under 35 U.S.C. 154(b) by 245 days.

(21) Appl. No.: 17/773,306

(22) PCT Filed: Oct. 23, 2020

(86) PCT No.: PCT/EP2020/025472
§ 371 (c)(1),
(2) Date: Apr. 29, 2022

(87) PCT Pub. No.: WO2021/083546
PCT Pub. Date: May 6, 2021

(65) Prior Publication Data
US 2022/0396539 A1   Dec. 15, 2022

(30) Foreign Application Priority Data
Oct. 31, 2019  (EP) ..................... 19020610

(51) Int. Cl.
*C07C 29/151*  (2006.01)
*C01B 3/38*  (2006.01)
*C07C 29/152*  (2006.01)

(52) U.S. Cl.
CPC .......... *C07C 29/1518* (2013.01); *C01B 3/382* (2013.01); *C07C 29/152* (2013.01); *C01B 2203/0244* (2013.01); *C01B 2203/061* (2013.01)

(58) Field of Classification Search
CPC . C07C 29/1518; C07C 29/152; C07C 29/151; C07C 31/04; C01B 3/382; C01B 2203/061; B01J 3/04
See application file for complete search history.

(56) References Cited

U.S. PATENT DOCUMENTS

| 7,786,180 | B2 | 8/2010 | Fitzpatrick |
| 2009/0018220 | A1* | 1/2009 | Fitzpatrick .............. C12C 11/02 518/700 |
| 2019/0047931 | A1 | 2/2019 | Balthasar et al. |

FOREIGN PATENT DOCUMENTS

| DE | 11 2006 001310 T5 | 4/2008 |
| EP | 3 205 622 | 8/2017 |

OTHER PUBLICATIONS

International Search Report and Written Opinion for corresponding PCT/EP2020/025472, dated Feb. 4, 2021.

* cited by examiner

*Primary Examiner* — Jafar F Parsa
(74) *Attorney, Agent, or Firm* — Elwood L. Haynes

(57) ABSTRACT

A process for producing methanol, wherein a make-up gas stream from a reformer unit is admixed with a hydrogen-containing stream from a hydrogen recovery stage to obtain a hydrogen-rich synthesis gas, which is combined with a residual gas stream and the combined stream is passed through a bed of a methanol synthesis catalyst at elevated pressure and elevated temperature to obtain a product stream comprising methanol and the residual gas stream and wherein the product stream is cooled to remove methanol (Continued)

from the residual gas stream. Wherein a portion of the residual gas stream is removed as a purge gas stream and a portion of the hydrogen-rich synthesis gas stream is removed and combined with the purge gas stream to obtain a mixed synthesis gas stream and the mixed synthesis gas stream is sent to the hydrogen recovery stage to produce the hydrogen-containing stream.

13 Claims, 3 Drawing Sheets

PROCESS AND PLANT FOR PRODUCING METHANOL FROM HYDROGEN-RICH SYNTHESIS GAS

CROSS REFERENCE TO RELATED APPLICATIONS

This application is a 371 of International Application No. PCT/EP2020/025472, filed Oct. 23, 2020, which claims priority to European Patent Application No. EP 19020610.2, filed Oct. 31, 2019, the entire contents of which are incorporated herein by reference.

FIELD OF THE INVENTION

The invention relates to a process and a plant for producing methanol from a hydrogen-poor make-up gas stream, wherein the hydrogen-poor make-up gas stream is admixed with a hydrogen-containing stream to obtain a hydrogen-rich synthesis gas stream having a stoichiometry number of not less than 2.0. The invention further relates to the use of the process according to the invention or of the plant according to the invention for producing methanol from make-up gas produced by autothermal reforming and/or partial oxidation.

BACKGROUND

On a large industrial scale methanol is produced from synthesis gas. Synthesis gas is a mixture of predominantly hydrogen ($H_2$), carbon monoxide (CO) and carbon dioxide ($CO_2$). It further comprises smaller amounts of gas constituents inert under the conditions of methanol synthesis. Carbon monoxide and carbon dioxide are often subsumed in the term "carbon oxides". In the process today described as low-pressure methanol synthesis the synthesis gas is converted into methanol and water (as a necessarily generated by-product) at a synthesis pressure of 60 to 120 bar. After compression to the respective synthesis pressure the employed synthesis gas, often referred to as make-up gas, is passed through a catalyst bed of a methanol synthesis catalyst at catalyst temperatures of typically more than 200° C. The methanol synthesis catalyst is typically a composition comprising copper as the catalytically active species. Depending on the process mode one or more serially arranged or parallel reactors, each having an appropriate catalyst bed, are employed. The conversion of the carbon oxides into methanol and water over the catalyst is incomplete on account of the establishment of a thermodynamic equilibrium according to the reactions

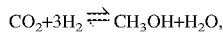

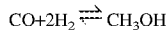

As a result the production process is typically run as a recirculating process in a so-called synthesis loop. The reaction mixture obtained at the reactor outlet is cooled to below the boiling point of methanol to remove methanol and water from the circuit. Unconverted synthesis gas is simultaneously recycled to the methanol synthesis catalyst for further reaction. A substream of unconverted synthesis gas is continuously withdrawn as a purge gas stream to avoid the concentration of inert constituents in the synthesis loop increasing over time.

The composition of the make-up gas or of a synthesis gas is generally characterized by the so-called stoichiometry number SN defined as $$SN = \frac{n(H_2) - n(CO_2)}{n(CO) + n(CO_2)}, n \text{ in [mol]}$$

A make-up gas composition stoichiometrically balanced for methanol synthesis is characterized by a stoichiometry number SN of 2.0. Values of less than 2.0 indicate a hydrogen deficit while values of greater than 2.0 indicate a hydrogen excess.

Synthesis gases having a hydrogen deficit are obtained for example in processes comprising a partial oxidation step or in the production of synthesis gas by coal gasification. In such a case the hydrogen is virtually completely consumed in the methanol synthesis while a substantial portion of the carbon oxides is not converted. This results in a composition in the synthesis loop which features high proportions of carbon oxides but a low proportion of hydrogen. This has the result, inter alia, that the methanol synthesis reactor is to be configured with a high catalyst volume and the content of by-products (especially higher alcohols and ketones) is higher than desired.

In order also to allow advantageous use of hydrogen-poor synthesis gas on a large industrial scale during methanol production, the synthesis gas may be adjusted to the desired stoichiometry number of not less than two using hydrogen from a hydrogen recovery plant for example. This is possible for example through hydrogen recovery from the purge stream.

EP 3 205 622 B1 discloses a process wherein unconverted synthesis gas referred to as residual gas is partially sent (as purge gas) to a hydrogen recovery stage. This affords a hydrogen-containing stream which is admixed with the make-up gas stream. The resulting mixture is subsequently compressed to synthesis pressure and converted into methanol.

However, the hydrogen amounts obtainable from the partial stream of the unconverted synthesis gas are often insufficient to obtain a synthesis gas having an adequately high stoichiometry number. For example synthesis gases having a high hydrogen deficit may require such a high purge stream proportion for hydrogen recovery that the synthesis loop must either be operated at low pressures or that the ratio of the recycle gas stream to the make-up gas stream must be set low.

To counter these disadvantages it is also conceivable to divert a portion of the make-up gas upstream of the methanol synthesis and send it to a hydrogen recovery stage. The disadvantage of this arrangement is that in the hydrogen recovery stage a portion of the hydrogen is lost before it passes into the synthesis circuit. Furthermore, after the enrichment with this hydrogen the synthesis gas has a stoichiometry number of more than two which can have the result that the purge gas stream not utilized in this case may comprise a considerable amount of unconverted hydrogen.

U.S. Pat. No. 7,786,180 B2 therefore proposes supplying the hydrogen recovery stage with a mixed stream of make-up gas and purge gas to at least partially overcome the abovementioned disadvantages. The disadvantage of this arrangement is for example that the make-up gas stream must be throttled by a pressure reduction valve in order at least to equalize the pressure drop generated by the hydrogen recovery stage. The pressure thus lost in the make-up gas conduit must be compensated in the subsequent compression to synthesis pressure.

SUMMARY

It is an object of the present invention to provide a process and a plant for producing methanol which at least partially overcomes the disadvantages of the prior art. It is especially an object of the present invention to provide a process and plant requiring no throttling of the main make-up gas stream through a pressure reducing apparatus.

The independent claims provide a contribution to the at least partial achievement of at least one of the abovementioned objects. The dependent claims provide preferred embodiments which contribute to the at least partial achievement of at least one of the objects. Preferred embodiments of constituents of a category according to the invention are, where relevant, likewise preferred for identically named or corresponding constituents of a respective other category according to the invention.

The terms "having", "comprising" or "containing" etc. do not preclude the possible presence of further elements, ingredients etc. The indefinite article "a" does not preclude the possible presence of a plurality.

The abovementioned objects are at least partially solved by a process for producing methanol, wherein a make-up gas stream from a reformer unit comprising hydrogen and carbon oxides is admixed with a hydrogen-containing stream from a hydrogen recovery stage to obtain a hydrogen-rich synthesis gas stream having a stoichiometry number SN, defined as $SN=[n(H_2)-n(CO_2)]/[n(CO)+n(CO_2)]$, of not less than 2.0 and wherein the hydrogen-rich synthesis gas stream is combined with a residual gas stream and the hydrogen-rich synthesis gas stream and the residual gas stream are passed through a bed of a methanol synthesis catalyst at elevated pressure and elevated temperature to obtain a product stream comprising methanol and the residual gas stream and wherein the product stream is cooled to remove methanol from the residual gas stream. According to the invention it is provided that a portion of the residual gas stream is removed as a purge gas stream and a portion of the hydrogen-rich synthesis gas stream is removed and combined with the purge gas stream to obtain a mixed synthesis gas stream and the mixed synthesis gas stream is sent to the hydrogen recovery stage to produce the hydrogen-containing stream.

The invention does not comprise sending the make-up gas stream and the purge gas stream diverted from the residual gas stream to the hydrogen recovery stage but on the contrary comprises sending the hydrogen-rich synthesis gas stream already adjusted with hydrogen to a stoichiometry number of not less than 2.0 to the hydrogen recovery stage together with the purge gas stream. This makes it possible to eschew a throttling of the make-up gas stream to divert a portion of the make-up gas stream in the direction of the hydrogen recovery stage. Investigations have further shown that the process mode according to the invention makes it possible to achieve savings in respect of the compression energy required.

The make-up gas stream is preferably a synthesis gas stream from a reformer unit which especially has a deficit of hydrogen and the stoichiometry number of the make-up gas is thus in particular less than 2.0. Such a make-up gas stream is especially produced in a reformer unit which comprises a partial oxidation step of a carbon-containing input gas to produce the synthesis gas. For example the make-up gas stream may be produced from autothermal reforming of a carbon-containing input gas. The input gas is preferably natural gas. The make-up gas stream may further be produced from coal gasification. Prior to the admixing of the hydrogen-containing stream and compression to synthesis pressure the make-up gas stream is cooled to a temperature of preferably not more than 40° C. for condensation and removal of water. The make-up gas stream typically has a pressure between 35 and 60 bar, which is why an additional compression to synthesis pressure is required prior to the conversion over the methanol synthesis catalyst.

A reformer unit may comprise a unit for conversion (reforming) of a gaseous carbon-containing input material or of a solid carbon-containing input material. One example of a gaseous carbon-containing input material is natural gas. Examples of solid carbon-containing input materials are coal, solid wastes (refuse) and biomass.

The hydrogen-containing stream preferably has a hydrogen content of not less than 95% by volume. A hydrogen-containing stream containing pure or substantially pure hydrogen is sought. In addition to the hydrogen-containing stream the hydrogen recovery stage also produces an offgas stream which comprises constituents inert under the conditions of the methanol synthesis and smaller amounts of unconverted carbon oxides.

The conversion of the hydrogen-rich synthesis gas stream and the residual gas stream to afford methanol (and water) is carried out over the methanol synthesis catalyst. The conversion is carried out in a synthesis loop, i.e. synthesis gas not converted over the catalyst is recycled as a residual gas stream to the inlet of the relevant reactor and converted into methanol over the methanol synthesis catalyst together with hydrogen-rich synthesis gas used for the first time. The conversion over the methanol synthesis catalyst is preferably carried out at a catalyst temperature of 220° C. to 270° C. and preferably a pressure of 55 bar to 80 bar. The conversion over the methanol synthesis catalyst is preferably carried out in one or more serially arranged or parallel reactor stages, wherein each of the reactor stages comprises an appropriate catalyst bed. The reactor stages especially comprise a water-cooled reactor and a gas-cooled reactor arranged downstream of the water-cooled reactor. Suitable catalysts are copper-based materials known from the prior art and comprising copper as the catalytically active species, one example thereof being a catalyst composition comprising copper, zinc oxide and aluminum oxide.

A preferred embodiment of the process according to the invention is characterized in that the hydrogen-rich synthesis gas stream is compressed and a portion of the compressed hydrogen-rich synthesis gas stream is removed and combined with the purge gas stream. The hydrogen-rich synthesis gas stream is preferably compressed to synthesis pressure. The hydrogen-rich synthesis gas stream is preferably compressed to a pressure of not less than 70 bar and not more than 90 bar. As investigations have shown and as is explained in detail hereinbelow, this type of process mode achieves savings in the required compression energy. It is preferable in this connection when the residual gas stream is compressed and combined with the compressed hydrogen-rich synthesis gas stream and the combined streams are passed through the bed of the methanol synthesis catalyst. The purge gas stream is especially diverted from the residual gas stream prior to the compression of the residual gas stream. The residual gas stream is preferably compressed to synthesis pressure. The residual gas stream is preferably compressed to a pressure of not less than 70 bar and not more than 90 bar.

A preferred embodiment of the process according to the invention is characterized in that the hydrogen-containing stream is compressed by a hydrogen compressor and the compressed hydrogen-containing stream is combined with the make-up gas stream to obtain the hydrogen-rich synthesis gas stream and a portion of the hydrogen-rich synthesis gas stream is removed and combined with the purge gas stream. As investigations have shown and as is explained hereinbelow, this type of process mode achieves savings in the required compression energy. The hydrogen-containing stream is compressed by the hydrogen compressor to a pressure which is about 1 to 2 bar above the pressure of the make-up gas (about 35 to 60 bar). It is preferable in this connection when the hydrogen-rich synthesis gas stream and the residual gas stream are compressed and passed through the bed of the methanol synthesis catalyst together. The hydrogen-rich synthesis gas stream and the residual gas stream are preferably compressed to synthesis pressure together. The hydrogen-rich synthesis gas stream and the residual gas stream are in particular compressed to a pressure of not less than 70 bar and not more than 90 bar together. The purge gas stream is thus necessarily diverted from the residual gas stream prior to the common compression of the residual gas stream and the hydrogen-rich synthesis gas stream.

A preferred embodiment of the process according to the invention is characterized in that the molar flow rate proportion of the hydrogen-rich synthesis gas stream in the mixed synthesis gas stream is between 0.10 and 0.95, preferably between 0.20 and 0.90, more preferably between 0.30 and 0.80 and more preferably between 0.50 and 0.75.

The molar flow rate may be reported for example in the units "kmol/h" (kilomol per hour).

A preferred embodiment of the process according to the invention is characterized in that the molar flow rate proportion of the portion removed from the hydrogen-rich synthesis gas stream based on the total molar flow rate of hydrogen-rich synthesis gas is between 0.001 and 0.999, preferably between 0.005 and 0.800, more preferably between 0.010 and 0.500, more preferably between 0.020 and 0.200 and more preferably between 0.050 and 0.100.

A preferred embodiment of the process according to the invention is characterized in that the hydrogen-rich synthesis gas stream has a stoichiometry number SN of 2.00 to 2.20, preferably of 2.02 to 2.10 and more preferably of 2.05 to 2.07.

A preferred embodiment of the process according to the invention is characterized in that the make-up gas stream has a stoichiometry number SN of less than 2.0, preferably of 1.70 to 1.95, more preferably of 1.75 to 1.90 and more preferably of 1.78 to 1.85. Synthesis gas from autothermal reforming often has a stoichiometry number around 1.80.

A preferred embodiment of the process according to the invention is characterized in that the hydrogen recovery stage comprises a pressure swing adsorption apparatus for removing hydrogen from the mixed synthesis gas stream. A pressure swing adsorption apparatus makes it possible to produce pure or at least virtually pure hydrogen at high pressures, for example at 40 to 60 bar. When hydrogen is already provided at high pressure by the hydrogen recovery stage, subsequent compressor stages, for example for compressing hydrogen (hydrogen compressor) or for compressing the hydrogen-rich synthesis gas stream, may be made correspondingly smaller. The concentration of inert constituents in the synthesis loop moreover increases ever slower the higher the purity of the hydrogen produced in the hydrogen recovery stage.

As an alternative to a pressure swing adsorption apparatus the hydrogen recovery stage may also comprise a membrane separation stage for removing hydrogen from the mixed synthesis gas stream. Likewise conceivable are combinations of one or more pressure swing adsorption apparatuses and one or more membrane separation stages.

A preferred embodiment of the process according to the invention is characterized in that the hydrogen-containing stream has a hydrogen proportion of at least 95% by volume, preferably of at least 99% by volume, more preferably of at least 99.5% by volume, more preferably of at least 99.9% by volume.

The abovementioned objects are further at least partially achieved by a plant for producing methanol comprising the following plant components in fluid connection with one another: A reformer unit for producing a make-up gas stream comprising hydrogen and carbon oxides; a hydrogen recovery stage for producing a hydrogen-containing stream, wherein the reformer unit and the hydrogen recovery stage are configured such that a hydrogen-rich synthesis gas stream having a stoichiometry number SN, defined as SN= $[n(H_2)-n(CO_2)]/[n(CO)+n(CO_2)]$, of not less than 2.0 is obtainable from the hydrogen-containing stream and the make-up gas stream; a reactor stage comprising a methanol synthesis catalyst bed, wherein the reactor stage is configured such that the hydrogen-rich synthesis gas stream and a residual gas stream may be passed through the methanol synthesis catalyst bed at elevated pressure and elevated temperature, thus making it possible to obtain a product stream comprising methanol and the residual gas stream; a cooling apparatus for cooling the product stream, wherein the cooling apparatus is configured such that methanol may be removed from the residual gas stream. According to the invention it is provided that the plant is configured such that a portion of the residual gas stream may be removed as a purge gas stream and a portion of the synthesis gas stream may be removed and combined with the purge gas stream, thus making it possible to obtain a mixed synthesis gas stream, and the mixed synthesis gas stream may be sent to the hydrogen recovery stage to produce the hydrogen-containing stream.

The abovementioned objects are moreover at least partially achieved by the use of the process according to the invention or of the plant according to the invention for producing methanol from make-up gas produced by autothermal reforming and/or partial oxidation.

BRIEF DESCRIPTION OF THE DRAWINGS

The invention is more particularly elucidated hereinbelow by way of two inventive examples and one comparative example without in any way limiting the subject-matter of the invention. Further features, advantages and possible applications of the invention will be apparent from the following description of the working examples in connection with the drawings and the numerical examples.

DETAILED DESCRIPTION OF THE PREFERRED EMBODIMENTS

Figure 1:
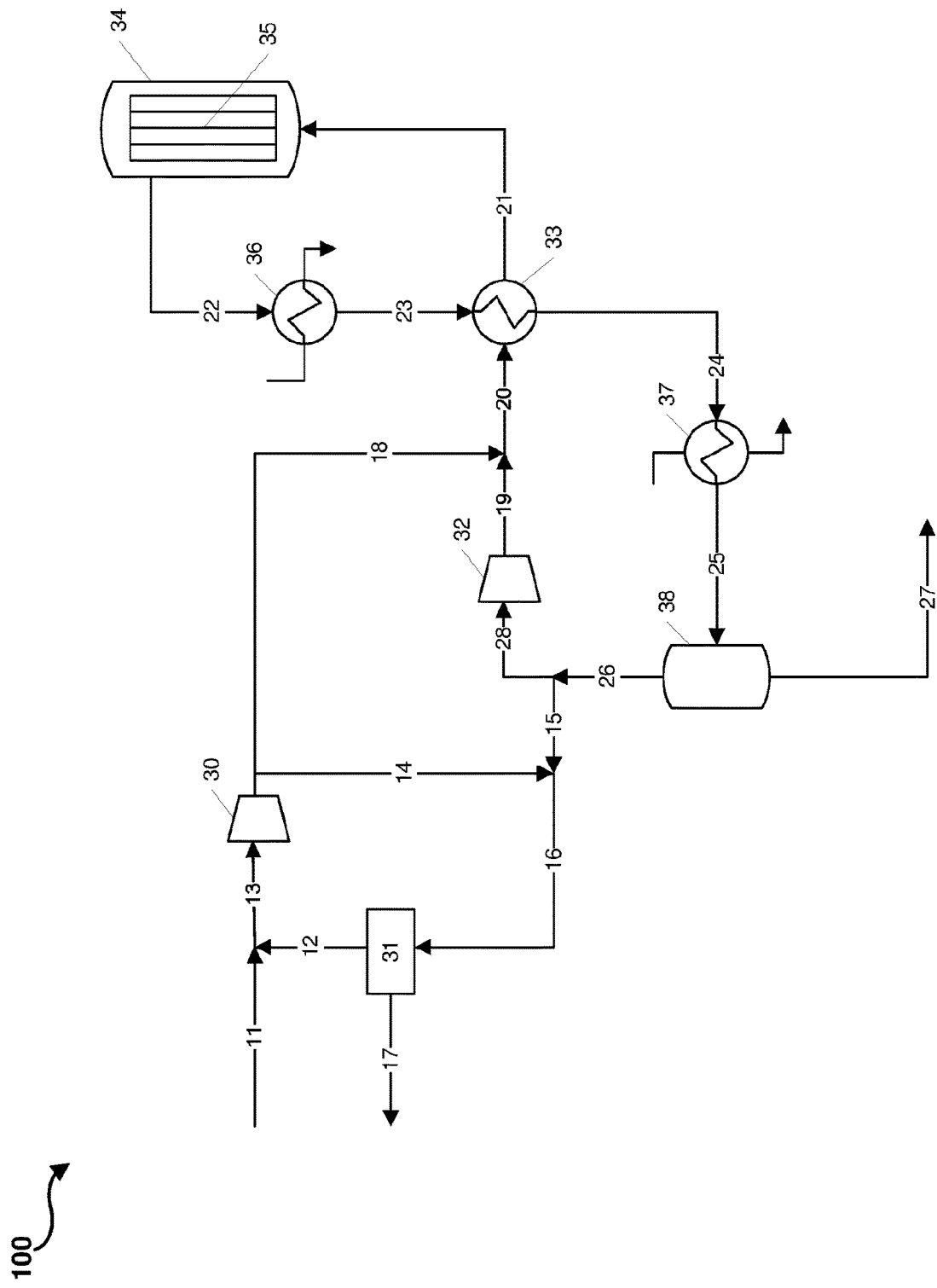
FIG. 1 shows a schematic block flow diagram of a production process or a plant 100 for methanol synthesis according to a first exemplary embodiment of the invention.

In the process mode according to FIG. 1 a make-up gas stream 11, for example produced in a plant for autothermal reforming of natural gas (not shown), is combined with a hydrogen-containing stream 12 to produce a hydrogen-rich synthesis gas stream 13 having a stoichiometry number of not less than 2.0. The hydrogen-rich synthesis gas stream 13 is compressed to synthesis pressure by a compressor stage 30. A portion of the hydrogen-rich synthesis gas stream 13 is removed as hydrogen-rich synthesis gas substream 14 and combined with a purge gas stream 15 to afford a mixed synthesis gas stream 16. The mixed synthesis gas stream 16 is sent to the hydrogen recovery stage 31, in which by pressure swing adsorption the hydrogen-containing stream 12 is produced with a hydrogen proportion of at least 99% by volume. Offgas 17 simultaneously produced in the hydrogen recovery stage 31 and containing carbon oxides and constituents inert under the conditions of the methanol synthesis may be used for example as a fuel gas in the reformer unit arranged upstream of the methanol synthesis.

The main portion 18 of the hydrogen-rich synthesis gas stream compressed to synthesis pressure is combined with a residual gas stream 19 compressed to synthesis pressure in a compressor stage 32. The resulting combined synthesis gas stream 20 is heated in a heat exchanger 33 and as heated synthesis gas stream 21 sent to a methanol reactor 34. The methanol reactor 34 carries out the conversion of the synthesis gas from synthesis gas stream 21 over the methanol synthesis catalyst of the catalyst bed 35 to afford methanol and water. The product stream 22 resulting from the conversion in the reactor 34 which comprises not only methanol and water but also unreacted synthesis gas or residual gas is then consecutively cooled via the heat exchangers 36, 33 and 37, the product streams 23, 24 and 25 resulting downstream of the respective heat exchangers. A separator 38 subsequently carries out the separation of the cooled product stream 25 into a liquid phase comprising methanol and water and a gaseous phase comprising residual gas. The synthesis gas not converted in the reactor 34, i.e. residual gas, is withdrawn from the separator 38 as residual gas stream 26. A crude methanol stream 27 comprising methanol and water is simultaneously withdrawn from the separator 38 and sent for further workup, for example a rectification (not shown). The purge gas stream 15 is removed from the residual gas stream 26 and a remaining residual gas stream 28 is compressed to synthesis pressure in the compressor stage 32. Residual gas stream 19 compressed to synthesis pressure is in turn combined with hydrogen-rich synthesis gas stream 18 and sent back to the conversion to afford methanol in the methanol reactor 34.

Figure 2:
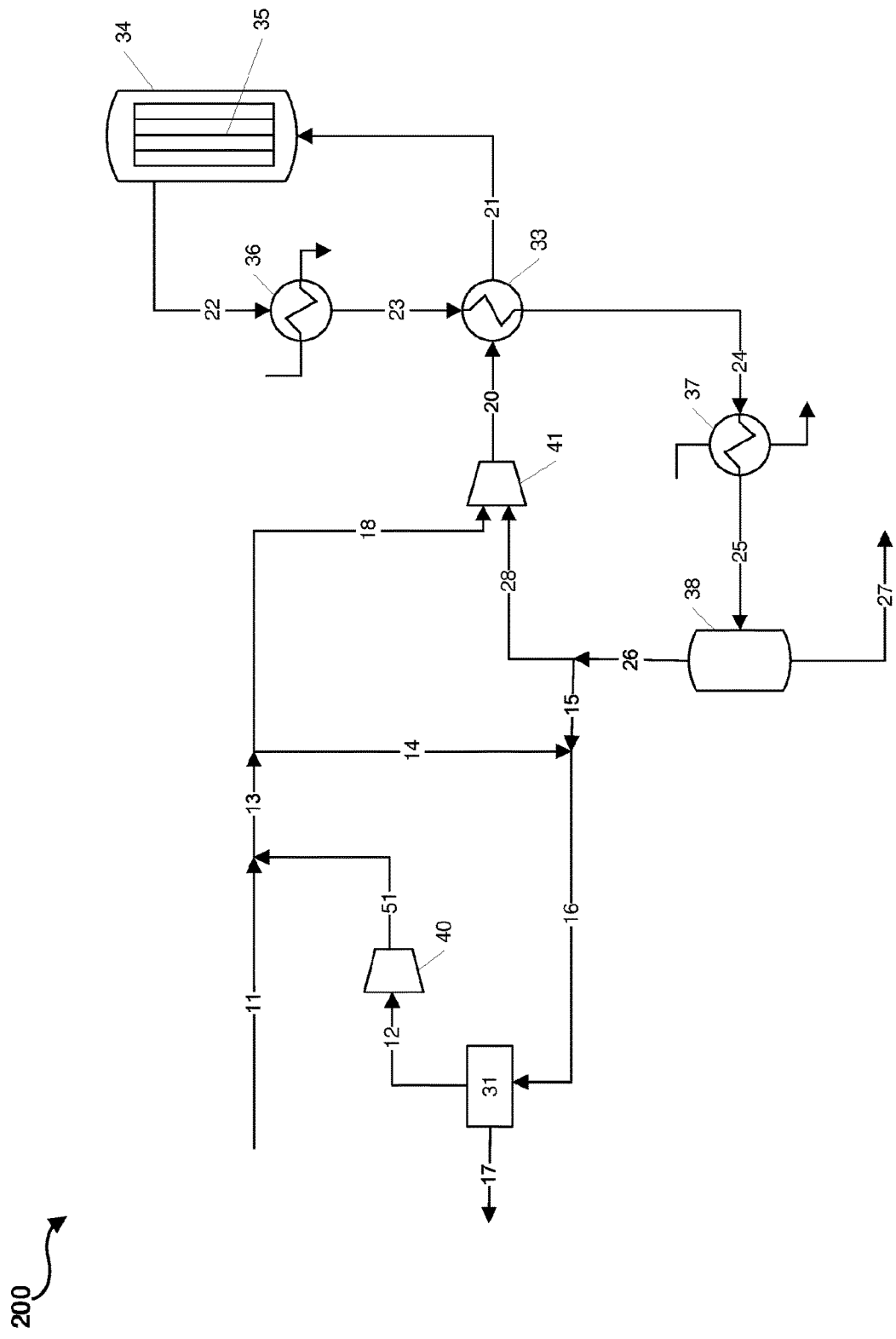
FIG. 2 shows a schematic block flow diagram of a production process or a plant 200 for methanol synthesis according to a second exemplary embodiment of the invention.

FIG. 2 shows a type of process mode according to a further inventive example which is modified compared to the example of FIG. 1. In the process mode according to FIG. 2 the hydrogen-containing stream 12 produced in the hydrogen recovery stage 31 is compressed in a hydrogen compressor 40 to obtain a compressed hydrogen-containing stream 51 which is combined with the make-up gas stream 11. This affords a hydrogen-rich synthesis gas stream 13 of which the main portion 18 is sent to compressor stage 41 for compression to synthesis pressure and of which a portion is diverted as hydrogen-rich synthesis gas substream 14 and combined with the purge gas stream 15. The mixed synthesis gas stream 16 results from the streams 14 and 15. The hydrogen-rich synthesis gas stream 18 and the residual gas stream are together sent to a compressor stage 41. Compressor stage 41 has two ports on its suction side which allows simultaneous compression of the hydrogen-rich synthesis gas stream 18 and the residual gas stream 28 to obtain the combined synthesis gas stream 20 which is heated in heat exchanger 33 and sent as synthesis gas stream 21 to the methanol reactor 34.

That which is recited in connection with FIG. 1 applies correspondingly to the further elements shown in FIG. 2.

Figure 3:
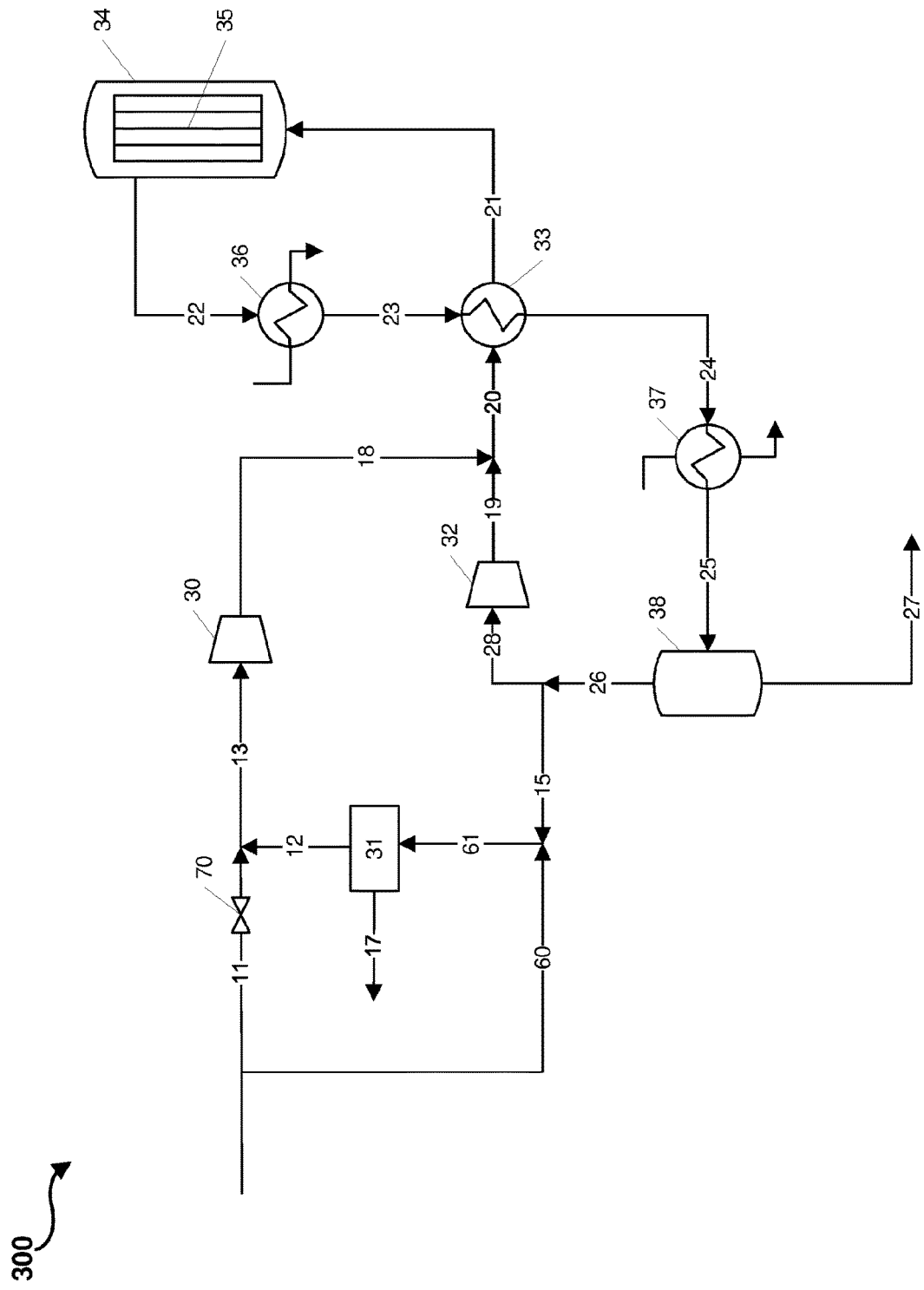
FIG. 3 shows a schematic block flow diagram of a production process or a plant 300 for methanol synthesis according to the prior art.

FIG. 3 shows a type of process mode known from the prior art. Here too, a mixed gas stream of synthesis gas and purge gas is sent to the hydrogen recovery stage 31 and utilized for hydrogen recovery. However, the synthesis gas proportion of the mixed gas stream is a partial make-up gas stream 60 which is diverted from the (main) make-up gas stream 11 using the throttle means 70. The partial make-up gas stream 60 and the purge gas stream 15 are recycled and as mixed synthesis gas stream 61 sent to the hydrogen recovery stage 31. In contrast to the above inventive examples the mixed synthesis gas stream 61 is thus not produced from synthesis gas already enriched with hydrogen and purge gas but rather from make-up gas and purge gas. However, as shown in the following numerical examples this type of process mode has disadvantages compared to the inventive process. One disadvantage results from the unavoidable use of the throttle means 70 required for throttling the (main) make-up gas stream 11. The reduction in pressure by the throttle means 70 must be compensated by compressor stage 30.

The advantages of the invention are hereinbelow illustrated using two numerical examples. Both examples represent simulated cases which were calculated using the simulation software "Aspen Plus".

EXAMPLES

Example 1

Example 1 is based on the process mode according to FIG. 1 in contrast with the process mode of the prior art (FIG. 3—comparative example).

According to Example 1 and the comparative example the hydrogen-poor synthesis gas stream or make-up gas stream (11) has the following composition:

| Component | Proportion (% by vol.) |
| --- | --- |
| Water | 0.21 |
| Carbon dioxide | 8.04 |
| Carbon monoxide | 23.16 |
| Hydrogen | 65.94 |
| Argon | 0.12 |
| Nitrogen | 0.52 |
| Methane | 2.01 |

For the hydrogen-poor synthesis gas stream or make-up gas stream this results in a stoichiometry number SN of 1.86.

Argon, nitrogen and methane are gas constituents inert under the conditions of the methanol synthesis and are discharged from the synthesis circuit substantially via the purge gas stream (15).

According to Example 1 and the comparative example the hydrogen-rich synthesis gas stream (13, 18) has the following composition:

| Component | Proportion (% by vol.) |
| --- | --- |
| Water | 0.19 |
| Carbon dioxide | 7.54 |
| Carbon monoxide | 21.71 |
| Hydrogen | 68.07 |
| Argon | 0.11 |
| Nitrogen | 0.49 |
| Methane | 1.89 |

For the hydrogen-rich synthesis gas stream this results in a stoichiometry number SN of 2.07.

The molar flow rate of hydrogen-rich synthesis gas (proportion 14 of the overall stream of the hydrogen-rich synthesis gas) sent to the hydrogen recovery stage (31) is 1451.5 kmol/h. The molar flow rate of the purge gas stream (15) is 1306.3 kmol/h. Both streams together form the mixed synthesis gas stream (16) having a molar flow rate of 2757.8 kmol/h. For Example 1 this results in a molar flow rate proportion or molar proportion of the hydrogen-rich synthesis gas stream in the mixed synthesis gas stream of 0.53.

According to Example 1 the molar flow rate proportion or molar proportion of the portion (14) removed from the hydrogen-rich synthesis gas stream based on the total molar flow rate of hydrogen-rich synthesis gas (13) is 0.059.

Compared to the process mode according to the comparative example (FIG. 3) for the same production quantity of crude methanol (crude methanol=mixture of methanol and water the following picture emerges in terms of energy consumption:

| Parameter | Comparative example (FIG. 3) | Example 1 (FIG. 1) |
| --- | --- | --- |
| Synthesis gas compressor power/KW | 16808 | 15791 |
| Mass flow natural gas for make-up gas production/kg/h | 126801 | 126801 |
| High-pressure steam export potential/kg/h | 247190 | 249861 |
| Crude methanol production/kg/h | 209266 | 209266 |
| Specific compressor power for compressor stage 30/kW/MT (MT = metric ton) | 80.32 | 75.46 |

The achieved energy savings in respect of the compressor power required for compression of the synthesis gas to synthesis pressure (compressor stage 30 in FIG. 1 and FIG. 3) results in an annual energy saving of 71867 GJ (71867 GJ/a). In addition the process mode according to Example 1 (FIG. 1) provides a higher potential for production of high-pressure steam as export steam.

Example 2

Example 2 is based on the process mode according to FIG. 2 in contrast with the process mode of the prior art (FIG. 3—comparative example).

According to Example 2 and the comparative example the hydrogen-poor synthesis gas stream or make-up gas stream (11) has the following composition:

| Component | Proportion (% by vol.) |
| --- | --- |
| Water | 0.16 |
| Carbon dioxide | 7.54 |
| Carbon monoxide | 24.68 |
| Hydrogen | 65.55 |
| Argon | 0.12 |
| Nitrogen | 0.09 |
| Methane | 1.86 |

For the hydrogen-poor synthesis gas stream or make-up gas stream this results in a stoichiometry number SN of 1.80.

According to Example 2 and the comparative example the hydrogen-rich synthesis gas stream (13, 18) has the following composition:

| Component | Proportion (% by vol.) |
| --- | --- |
| Water | 0.14 |
| Carbon dioxide | 6.99 |
| Carbon monoxide | 22.84 |
| Hydrogen | 68.12 |
| Argon | 0.11 |
| Nitrogen | 0.08 |
| Methane | 1.72 |

For the hydrogen-rich synthesis gas stream this results in a stoichiometry number SN of 2.05.

The molar flow rate of hydrogen-rich synthesis gas (proportion 14 of the overall stream of the hydrogen-rich synthesis gas) sent to the hydrogen recovery stage (31) is 2280.0 kmol/hr. The molar flow rate of the purge gas stream (15) is 976.4 kmol/hr. Both streams together form the mixed synthesis gas stream (16) having a molar flow rate of 3256.4 kmol/hr. For Example 2 this results in a molar flow rate proportion or molar proportion of the hydrogen-rich synthesis gas stream in the mixed synthesis gas stream of 0.70.

According to Example 2, the molar flow rate proportion or molar proportion of the portion (14) removed from the hydrogen-rich synthesis gas stream based on the total molar flow rate of hydrogen-rich synthesis gas (13) is 0.091.

Compared to the process mode according to the comparative example (FIG. 3) for the same production quantity of crude methanol (crude methanol=mixture of methanol and water) the following picture emerges in terms of energy consumption:

| Parameter | Comparative example (FIG. 3) | Example 2 (FIG. 2) |
| --- | --- | --- |
| Synthesis gas compressor power/KW | 10756 | 8797 |
| Hydrogen compressor power | n/a | 84 |
| Mass flow natural gas for make-up gas production/kg/h | 131664 | 131147 |
| Crude methanol production/kg/h | 209394 | 209394 |
| Specific compressor power for compressor stage 30/kW/MT (MT = metric ton) | 51.37 | 42.42 |

The achieved energy savings in respect of the compressor power required for compression of the synthesis gas to synthesis pressure (compressor stage 30 in FIG. 3; synthesis gas proportion compressor stage 41 and hydrogen compressor 40 in FIG. 2) results in an annual energy saving of 206548 GJ (206548 GJ/a).

LIST OF REFERENCE NUMERALS 100, 200 Process, plant (invention)
300 Process, plant (prior art)
11 Make-up gas stream
12, 51 Hydrogen-containing stream
13, 18 Hydrogen-rich synthesis gas stream
14 Hydrogen-rich synthesis gas substream
15 Purge gas stream 16 Mixed synthesis gas stream (invention)
17 Offgas
19, 26, 28 Residual gas stream
20 Combined synthesis gas stream
21 Synthesis gas stream
22, 23, 24, 25 Product stream
26 Residual gas stream
27 Crude methanol stream
30, 32, 41 Compressor stage
31 Hydrogen recovery stage
33, 36, 37 Heat exchanger
38 Separator
40 Hydrogen compressor
60 Partial make-up gas stream
61 Mixed synthesis gas stream (prior art)
70 Throttle means It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

The invention claimed is:

1. A process for producing methanol, wherein a make-up gas stream from a reformer unit comprising hydrogen and carbon oxides is admixed with a hydrogen-containing stream from a hydrogen recovery stage to obtain a hydrogen-rich synthesis gas stream having a stoichiometry number SN, defined as $SN=[n(H_2)-n(CO_2)]/[n(CO)+n(CO_2)]$, of not less than 2.0 and wherein the hydrogen-rich synthesis gas stream is combined with a residual gas stream and the hydrogen-rich synthesis gas stream and the residual gas stream are passed through a bed of a methanol synthesis catalyst at elevated pressure and elevated temperature to obtain a product stream comprising methanol and the residual gas stream and wherein the product stream is cooled to remove methanol from the residual gas stream,
wherein:
a portion of the residual gas stream is removed as a purge gas stream and
a portion of the hydrogen-rich synthesis gas stream is removed and combined with the purge gas stream to obtain a mixed synthesis gas stream and the mixed synthesis gas stream is sent to the hydrogen recovery stage to produce the hydrogen-containing stream.

2. The process according to claim 1, wherein the hydrogen-rich synthesis gas stream is compressed and a portion of the compressed hydrogen-rich synthesis gas stream is removed and combined with the purge gas stream.

3. The process according to claim 2, wherein the residual gas stream is compressed and combined with the compressed hydrogen-rich synthesis gas stream and the combined streams are passed through the bed of the methanol synthesis catalyst.

4. The process according to claim 1, wherein the hydrogen-containing stream is compressed by a hydrogen compressor and the compressed hydrogen-containing stream is combined with the make-up gas stream to obtain the hydrogen-rich synthesis gas stream and a portion of the hydrogen-rich synthesis gas stream is removed and combined with the purge gas stream.

5. The process according to claim 4, wherein the hydrogen-rich synthesis gas stream and the residual gas stream are compressed and passed through the bed of the methanol synthesis catalyst together.

6. The process according to claim 1, wherein the molar flow rate proportion of the hydrogen-rich synthesis gas stream in the mixed synthesis gas stream is between 0.10 and 0.95.

7. The process according to claim 1, wherein the molar flow rate proportion of the portion removed from the hydrogen-rich synthesis gas stream based on the total molar flow rate of hydrogen-rich synthesis gas is between 0.001 and 0.999.

8. The process according to claim 1, wherein the hydrogen-rich synthesis gas stream has a stoichiometry number SN of 2.00 to 2.20.

9. The process according to claim 1, wherein the make-up gas stream has a stoichiometry number SN of less than 2.0.

10. The process according to claim 1, wherein the hydrogen recovery stage comprises a pressure swing adsorption apparatus for removing hydrogen from the mixed synthesis gas stream.

11. The process according to claim 1, wherein the hydrogen recovery stage comprises a membrane separation stage for removing hydrogen from the mixed synthesis gas stream.

12. The process according to claim 1, wherein the hydrogen-containing stream has a hydrogen proportion of at least 95% by volume.

13. A plant for producing methanol comprising the following plant components arranged in fluid connection with one another:
a reformer unit for producing a make-up gas stream comprising hydrogen and carbon oxides;
a hydrogen recovery stage for producing a hydrogen-containing stream, wherein the reformer unit and the hydrogen recovery stage are configured such that a hydrogen-rich synthesis gas stream having a stoichiometry number SN, defined as $SN=[n(H_2)-n(CO_2)]/[n(CO)+n(CO_2)]$, of not less than 2.0 is obtainable from the hydrogen-containing stream and the make-up gas stream;
a reactor stage comprising a methanol synthesis catalyst bed, wherein the reactor stage is configured such that the hydrogen-rich synthesis gas stream and a residual gas stream may be passed through the methanol synthesis catalyst bed at elevated pressure and elevated temperature,
the reformer unit, the hydrogen recovery stage, and the reactor stage configured to produce a product stream comprising methanol and the residual gas stream;
a cooling apparatus for cooling the product stream, wherein the cooling apparatus is configured such that methanol may be removed from the residual gas stream,
wherein:
the plant is configured such that a portion of the residual gas stream may be removed as a purge gas stream and a portion of the synthesis gas stream may be removed and combined with the purge gas stream, thus making it possible to obtain a mixed synthesis gas stream, and the mixed synthesis gas stream may be sent to the hydrogen recovery stage to produce the hydrogen-containing stream.

* * * * *